(12) United States Patent
Cesmeli

(10) Patent No.: US 6,438,196 B1
(45) Date of Patent: Aug. 20, 2002

(54) EKG DRIVEN CT IMAGE RECONSTRUCTION FOR CARDIAC IMAGING

(75) Inventor: Erdogan Cesmeli, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/681,942

(22) Filed: Jun. 28, 2001

(51) Int. Cl.$^7$ ................................................ A61B 6/00
(52) U.S. Cl. .................................. 378/8; 378/4; 378/20
(58) Field of Search ........................... 378/8, 4, 20, 95; 600/509, 428

(56) References Cited

U.S. PATENT DOCUMENTS

| | | | |
|---|---|---|---|
| 4,510,944 A | * 4/1985 | Porges | 600/484 |
| 4,868,747 A | 9/1989 | Mori et al. | |
| 4,994,965 A | * 2/1991 | Crawford et al. | 324/309 |
| 5,195,525 A | 3/1993 | Pelc | |
| 5,662,109 A | 9/1997 | Hutson | |
| 5,669,385 A | * 9/1997 | Pesque et al. | 128/916 |
| 5,718,235 A | 2/1998 | Golosarsky et al. | |
| 5,891,044 A | 4/1999 | Golosarsky et al. | |
| 5,897,496 A | 4/1999 | Watanabe | |
| 5,953,388 A | * 9/1999 | Walnut et al. | 378/4 |
| 6,002,738 A | * 12/1999 | Cabral et al. | 378/15 |
| 6,014,419 A | * 1/2000 | Hu | 378/4 |
| 6,073,046 A | * 6/2000 | Patel et al. | 128/903 |
| 6,088,611 A | 7/2000 | Lauterbur et al. | |
| 6,231,834 B1 | 5/2001 | Unger et al. | |
| 6,233,478 B1 | 5/2001 | Liu | |
| 6,252,924 B1 | 6/2001 | Davantes et al. | |
| 6,256,368 B1 | * 7/2001 | Hsieh et al. | 378/8 |
| 6,275,560 B1 | 8/2001 | Blake et al. | |
| 6,307,910 B1 | 10/2001 | Acharaya et al. | |

* cited by examiner

Primary Examiner—David V. Bruce
Assistant Examiner—Pamela R. Hobden
(74) Attorney, Agent, or Firm—Armstrong Teasdale LLP

(57) ABSTRACT

A method for reconstructing an image of a beating heart includes decomposing at least one electrocardiogram (EKG) RR interval, tagging projection data with cardiac phase information based on the decomposition, and reconstructing an image using the tagged data.

32 Claims, 3 Drawing Sheets

EKG DRIVEN CT IMAGE RECONSTRUCTION FOR CARDIAC IMAGING

BACKGROUND OF INVENTION

This invention relates generally to computed tomography (CT) imaging, and more particularly to reliable cardiac imaging using a CT system.

The dynamic nature of a heart, and temporal and spatial resolution requirements for reliable diagnosis, make cardiac imaging a challenging task for CT technology. Specifically, as a CT gantry rotates, the heart continues to beat and move, and projection data is collected at varying cardiac phases. Since projection data cannot be acquired instantaneously, so that the cardiac phase of the heart is known for each projection data set, electrocardiograph (EKG) data is collected to correlate, or 'tag', CT projection data with cardiac phase information. The cardiac phase information is obtained by dividing each cardiac cycle of the EKG signal into sections that represent the different cardiac phases. One cardiac cycle within an EKG signal is understood to be represented by the part of the signal plotted from one R peak to the next R peak, i.e., the RR interval.

Typically, cardiac phases are determined by temporally dividing the RR interval in a linear fashion. There is an assumption that the duration of events in the RR interval scale linearly when the heart rate changes. However, when the heart rate changes, the different cardiac phases do not change linearly. Thus, temporal based, or linearly scaled, cardiac phase determination is not always accurate as the heart rate changes.

Projection data acquired from multiple rows of detectors are pre-processed to tag each view with z-location information and with the cardiac phase information. Projection data are selectively combined from multiple cardiac cycles for image reconstruction at specified z-locations and cardiac phases. Inaccuracies due to heart rate changes, however, impact the temporal and spatial resolution of the resulting image.

SUMMARY OF INVENTION

In one aspect, a method is provided for reconstructing an image of a beating heart. The method includes decomposing at least one electrocardiogram (EKG) RR interval such that the EKG RR interval is separated into constituent parts. Furthermore the method includes tagging projection data with cardiac phase information based on the decomposition, and reconstructing an image using the tagged data.

In another aspect, a system is provided for reconstructing an image of a beating heart. The system includes an electrocardiogram (EKG) device, a computed tomography (CT) device electrically coupled to the EKG device, and a processor electrically coupled to at least one of the EKG device and the CT device. Furthermore, the system is configured to decompose at least one electrocardiogram (EKG) RR interval, determine cardiac phase information based on the decomposition, and reconstruct an image using the phase information.

In yet another aspect, a computer readable medium encoded with a program executable by a computer, is provided for reconstructing images of a beating heart utilizing data gathered using a computed tomography (CT) device and an electrocardiogram (EKG) device. The program instructs the computer to decompose at least one EKG RR interval into at least one of a P wave, a Q wave, a R wave, a S wave, and a T wave, and tag projection data with cardiac phase information based on the decomposition.

In still another aspect, a method is provided for determining cardiac phase information used to reconstruct an image of a beating heart. The method includes decomposing at least one EKG RR interval and determining cardiac phase information based on the decomposition.

DETAILED DESCRIPTION

As used herein, the term "tagging" means correlating, or associating, positional and/or cardiac phase data with the scan data. Such tagging is performed by storing the positional or cardiac phase data with the scan data itself (e.g., as a digital word) or by storing positional or cardiac phase data in a table that is correlated to the scan data. Additionally, the term "decomposing" means separating an EKG signal, or a portion of the EKG signal, into constituent parts, such as a P wave, a Q wave, a R wave, a S wave, or a T wave. As described herein, the EKG signal is decomposed using a wavelet transform, such as the wavelet transform described in Detection of ECG Characteristic Points Using Wavelet Transforms, by C. Li, C. Zheng, and C. Tai, IEEE Transactions on Biomedical Engineering, Vol. 42, No. 1, January 1995.

Additionally, used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features. Also as used herein, the phrase "reconstructing an image" is not intended to exclude embodiments of the present invention in which data representing an image is generated but a viewable image is not. However, many embodiments generate (or are configured to generate) a viewable image.

Figure 1:
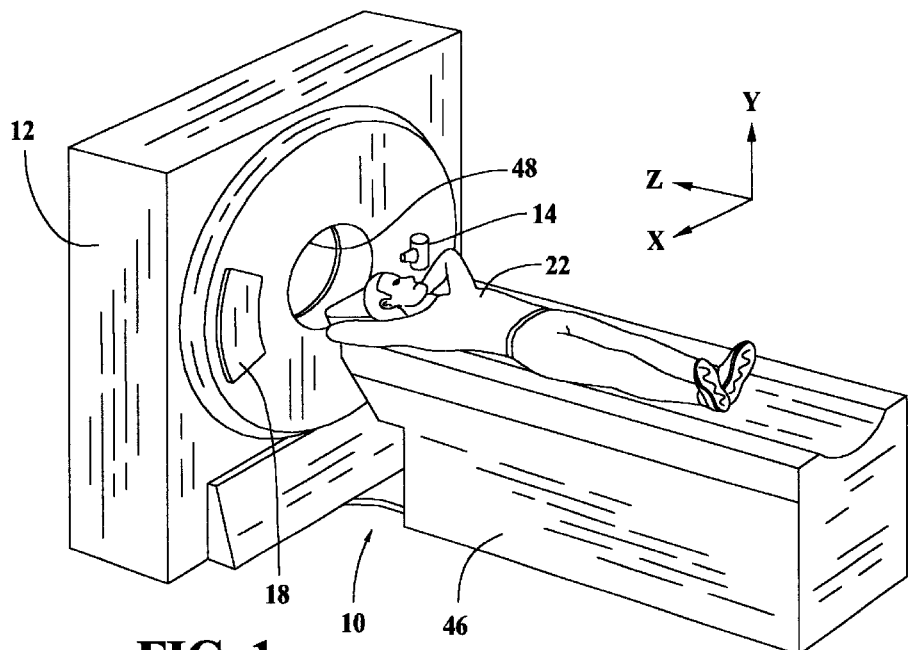
FIG. 1 is a pictorial view of a CT imaging system.
Figure 2:
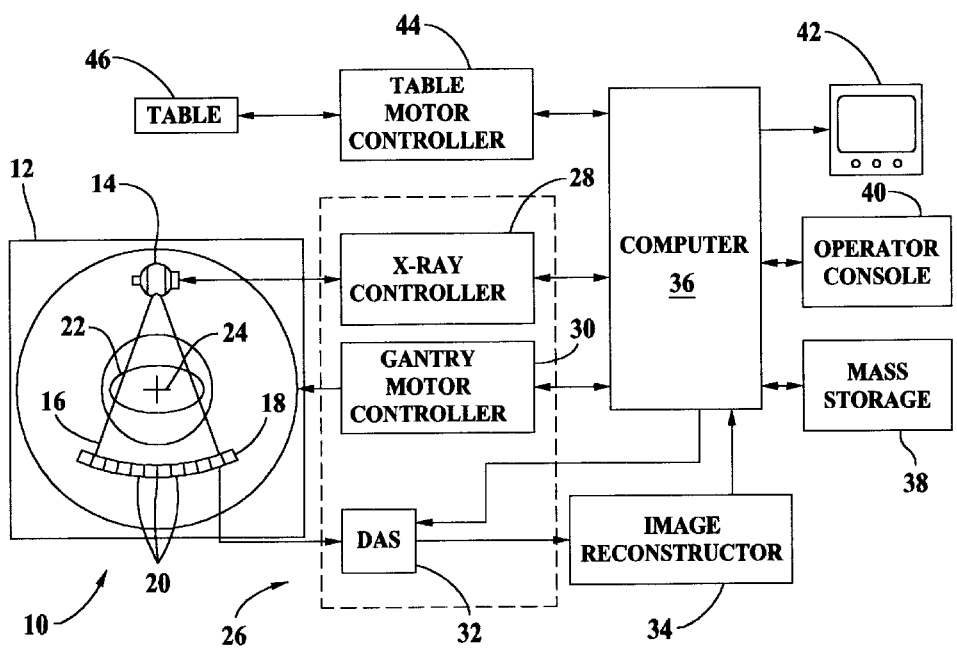
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20, which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36, which stores the image in a mass storage device 38, or outputs to a recording device (not shown), such as a film recorder. When an image is stored in storage device 38, the image may be stored as a data array, a linked list, or any other known data storage configurations. Computer 36 typically comprises a processor (not shown) and a memory device (not shown). The memory device may store a program, or algorithm, (not shown) comprising instructions for executing a process of the present invention. Alternatively, such a program may be executed, in whole or in part, by reconstructor 34, or by another computer system (not shown) included in, or coupled to, imaging system 10.

Computer 36 also receives commands and scanning parameters from an operator via console 40 that has a keyboard. An associated cathode ray tube display 42 allows the operator to observe the reconstructed image and other data from computer 36. In another embodiment, the reconstructed image may be transmitted as image data over a network (not shown) for disposition at another location. The operator supplied commands and parameters are used by computer 36 to provide control signals and information to DAS 32, x-ray controller 28 and gantry motor controller 30. In addition, computer 36 operates a table motor controller 44, which controls a motorized table 46 to position patient 22 in gantry 12. Particularly, table 46 moves portions of patient 22 through gantry opening 48.

X-ray source 14 projects a fan-shaped beam which is collimated to lie within an X-Y plane of a Cartesian coordinate system and generally referred to as the "imaging plane". The x-ray beam passes through the subject, such as a human patient or an animal patient. In either of these cases, the object to be imaged may be the entire subject, or an organ or body part of the subject. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

The x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle and at a single axial position is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. In a "helical" scan, the patient or object is moved while the data for the prescribed number of slices is acquired, thereby generating a single helix from a one fan beam helical scan. The helix mapped out by the fan beam yields projection data from which images in each prescribed slice may be reconstructed.

Cardiac reconstruction in multislice volume CT provides a three dimensional (3D) image of a beating heart at a given cardiac phase where the 3D volume is formed by a stack, or sequence, of parallel axial images. Helical scanning provides more axial coverage for a given patient breath-hold time. Therefore, the image reconstruction method and system described below are based on a protocol employing helical projections. However, the method and system are not limited to practice with helical scans, and other scan types, including, but not limited to an axial scan, can be employed. Additionally, system 10 is described herein by way of example only, and the image reconstruction method and system described below can be practiced in connection with many other types of imaging systems, for example, cine scan data. Furthermore, the image reconstruction method, or algorithm, described herein is typically performed by image reconstructor 34. Such method, however, could be implemented in other components of the imaging system such as in computer 36.

Figure 3:
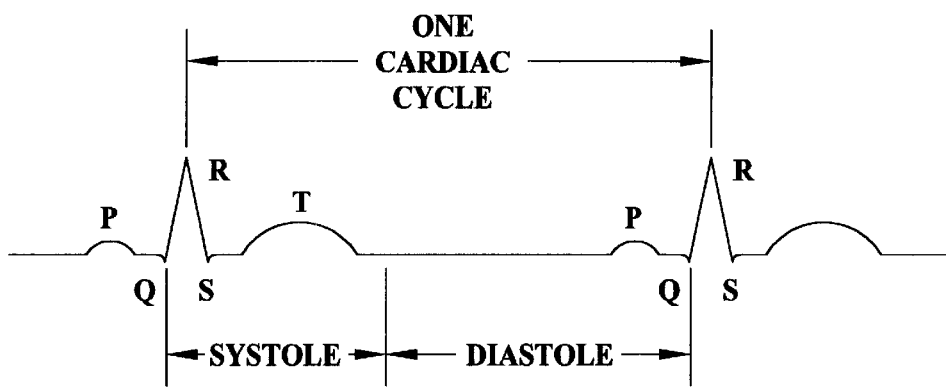
FIG. 3 is a representation of an EKG signal waveform.

FIG. 3 illustrates one cardiac cycle for an EKG signal waveform, including a systole phase, and a diastole phase, of the heart. The portions of the EKG signal labeled Q, R and S are referred to as a QRS complex, in which the R-feature, or R-wave, is the most prominent, highest amplitude, feature of the entire EKG signal. The cardiac cycle is typically defined as beginning with an R-wave and continuing until the occurrence of a next R-wave. The graphical representation of an EKG signal includes the QRS complex, a T wave, and a P wave. Analyzing the EKG signal with respect the QRS complex, the T wave, and the P wave allows more accurate phase information to be correlated with projection data as the heart rate changes.

In one embodiment, imaging system 10 generates at least one image of an object in a defined condition, or state. For example, system 10 generates a series of images of a patient's beating heart in vivo. In one embodiment, a wavelet transform is used to separate each RR interval into constituent parts, or sub-waves. More specifically, the wavelet transform decomposes each RR interval into P, Q, R, S, and T waves from which cardiac phase information is generated. The collected projection data is then tagged with the cardiac phase information. The tagged projection data are then combined from multiple cardiac cycles using any of several known multi-sector algorithms to reconstruct an image, such as the filtered back projection technique described in, Principles of Computerized Tomographic Imaging, by A. C. Kak and M. Slaney, IEEE Press, New York N.Y., 1988.

The term cardiac state is used herein in relation to temporal points in the periodic cardiac motion that are defined with respect to the individual sub-waves, within the EKG signal. The term cardiac phase is used herein in relation to temporal points in the periodic cardiac motion that are defined only in relation to the R peaks. Both terms relate to temporal points in the periodic cardiac motion, and are only distinguished by the manner in which the temporal points are defined. Therefore, when the process of tagging projection data with cardiac phase information is discussed herein with respect to the present invention, the terms are interchangeable.

In the example embodiment, a cardiac CT scan is performed to acquire projection data from detector array 18 as table 46 moves a patient through gantry 12 at a fixed speed. A single projection data set produced by each detector element 20, for a given position of gantry 12, is generally referred to as a 'view'. As projection data is acquired while table 46 moves in the z-direction, each view is correlated, or 'tagged', with z-location information. In one embodiment, computer 36 computes the z-location information and tags each view using information communicated from detector array 18, table motor controller 44 and gantry 12. For example, computer 36 utilizes the starting z-location of detector array 18, the period of gantry 12 and the table speed generated by motor controller 44 to compute a z-location for a corresponding view.

In addition to tagging each view with z-location information, system 10 tags each view with corresponding cardiac phase information. The corresponding cardiac phase information is determined by decomposing the EKG signal, collected simultaneously with the projection data, into a plurality of sub-waves and analyzing the sub-waves to determine cardiac state, or phase, information.

Figure 4:
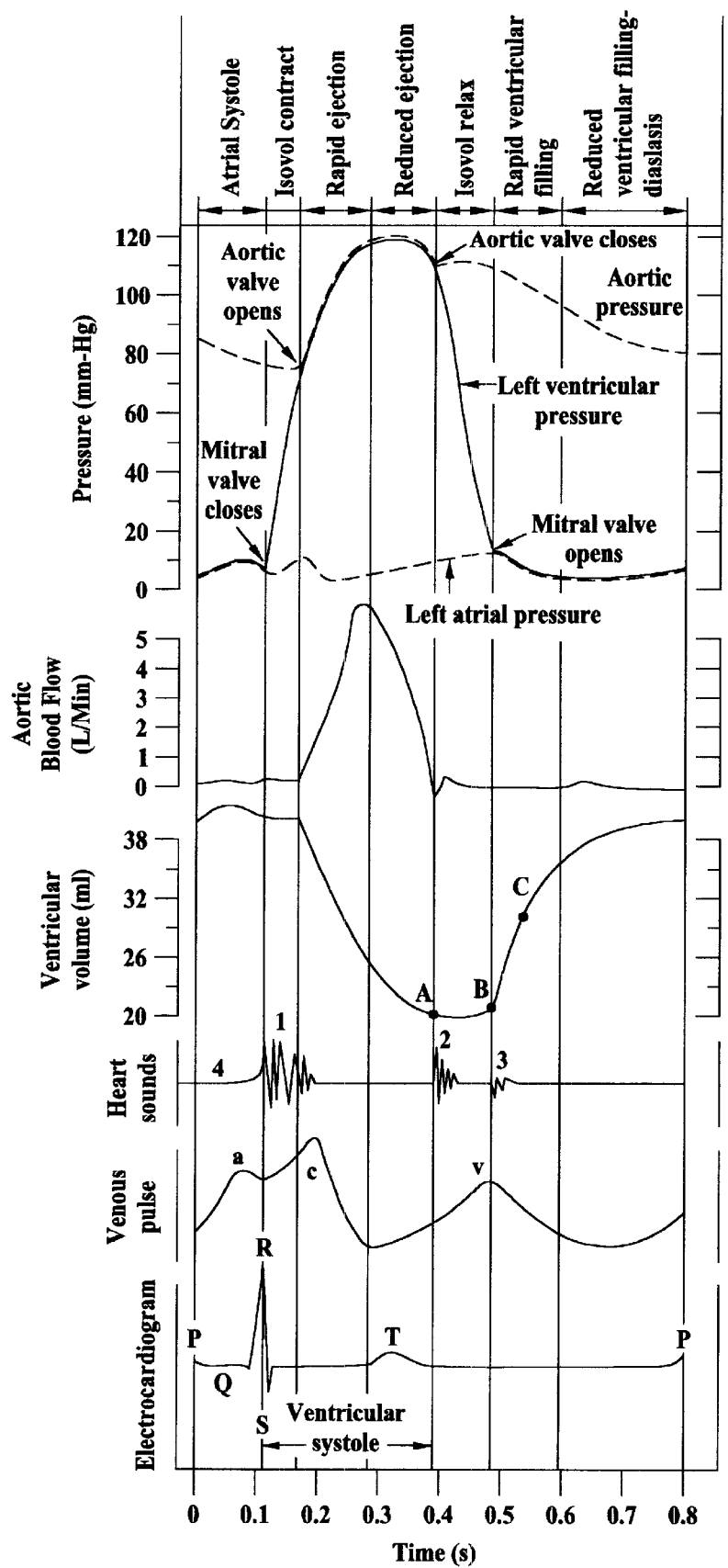
FIG. 4 is a graphical representation of a left atrial, aortic, and left ventricular pressure pulses correlated in time with various other monitored cardiac characteristics.

FIG. 4 is a graphical representation of left atrial, aortic and left ventricular pressure pulses correlated in time with various other monitored cardiac characteristics, such as aortic flow, ventricular volume, heart sounds, venous pulse, and an EKG. When the heart rate increases, it is not the entire RR interval that decreases in duration. More specifically, only the interval of reduced ventricular filling diaslasis gets shorter. Additionally, neighboring instances in time, such as points A, B, and C, may not correspond to the same cardiac phase. For example, although points A, B, and C are equally separated in time on the ventricular volume curve, they do not all belong to the same cardiac phase. Points A and B are in the isovolumic relaxation phase, while point C is in the rapid ventricular filling phase. The cardiac phases within a single cardiac cycle are non-linear and do not scale equally with heart rate variations.

Therefore, in order to tag projection views with accurate cardiac phase information, system 10 determines cardiac phase information by analyzing the actual behavior, or motion, of the heart as projection data is acquired. This analysis allows projection views to be tagged with more accurate cardiac phase information. More specifically, an algorithm is executed that utilizes wavelet transforms to analyze an EKG and determine the P, Q, R, S, and T waves within each cardiac cycle. In one embodiment, the algorithm is executed by reconstructor 34 (shown in FIG. 2) and stored in a storage device included in reconstructor 34. In an alternate embodiment, the algorithm is stored in mass storage device 38 (shown in FIG. 2) and executed by computer 36 (shown in FIG. 2).

Figure 5:
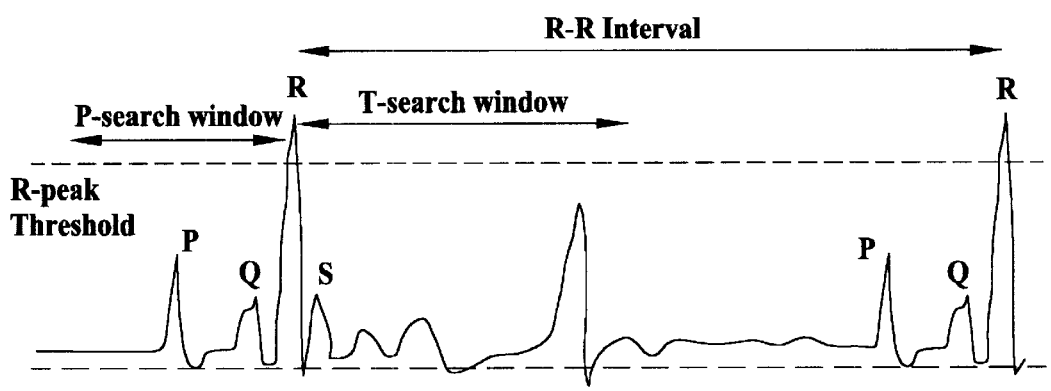
FIG. 5 is a representation of an EKG signal and illustrates application of a wavelet transform.

With respect to the algorithm, FIG. 5 represents an EKG signal and illustrates using a wavelet transform to determine the P, Q, R, S, and T waves, also referred to as the P peak, Q peak, R peak, S peak, and the T peak. More specifically, a dyadic quadratic spline wavelet transformation is performed on the EKG signal. Such a transform is described in, Detection of ECG Characteristic Points Using Wavelet Transforms, IEEE Transactions on Biomedical Engineering, Vol. 42, NO. 1, January 1995. In order to determine the R peaks in the EKG, zero crossings are detected. The most prominent peaks in the EKG are detected by finding a modulus maximum line. The moduli at zero crossings are calculated by the product of the minimum and maximum values that are on either side of the zero crossing. After finding the global maximum of these products, an R peak threshold of the global maximum is selected, for example 40%. Locations with moduli larger than the threshold are identified as R peaks. To avoid a false positive, maximum moduli from consecutive R peaks are compared. When the difference is larger than the global average maximum modulus, R peaks with smaller values are deleted from the R peak list. Next, a search window for P peaks is considered. The search window for the P peaks precedes each R peak. The size of the search window for the P peak is set adaptively based on the RR interval. The location with maximum modulus within the P peak search window is identified as the P peak. Similarly, T peaks are determined in a search window succeeding each R peak. The size of this R peak search window is also set according to the RR interval. Finally, the maximum moduli locations just before and after each R peak are taken as Q and S peaks respectively.

Generally, a wavelet transform is defined as a group, or bank, of filters applied to a signal, such as an EKG signal. A wavelet transform decomposes signals, such as an EKG signal, into elementary building blocks that are well localized in both time and frequency. Thus, the wavelet transform filters, or extracts, a plurality of frequency bands from the EKG signal that relate to the different cardiac states within the cardiac cycle, i.e. the atrial systole, isovolumic contractions, rapid ejection, reduced ejection, isovolumic relaxation, rapid ventricular filling, and reduced ventricular filling diastasis states. A single frequency band is selected from the different frequency bands and used to locate separate sub-waves within the EKG signal, that represent the behavior, or motion, of the heart during the different cardiac states.

The filter bank includes a plurality of filters, or wavelets, that are each applied to the EKG signal and produce a number of wavelet outputs, or filtered EKG signals. The number of filtered signals is equal to the number of wavelets in the wavelet transform, i.e., the number of wavelets in the filter bank.

Initially the EKG signal is filtered using a first, or 'mother', wavelet, such as a quadratic spline. A plurality of second, or derived, wavelets are determined by scaling the mother wavelet multiple times, for example by applying a dyadic scaling technique to the mother wavelet. The scaling of the mother wavelet results in the filter bank having a plurality of wavelets, for example 10, including the mother wavelet and the derived wavelets. Thereafter, the wavelet transform is applied to the EKG signal such that the EKG signal is filtered by the wavelets, thereby producing a plurality of outputs, or frequency bands. From the plurality of frequency bands a single frequency band, for example, the sixth scaled frequency band, is selected and used to locate sub-waves of the EKG signal, i.e., the P, Q, R, S, and T waves. The single frequency band is selected based on the closeness with which characteristics of the frequency band match the characteristics of the EKG signal.

To locate the sub-waves of the EKG signal, peaks in the selected frequency band are identified. The peaks in the selected frequency band correlated to the peaks in the EKG signal thereby locating the sub-waves of the EKG signal. To identify the peaks of the selected frequency band, a multiscale edge detection technique is used, such as multiscale edge technique described in Characterization of Signals from Multiscale Edges, by S. Mallat and S Zhong, IEEE Transactions on Pattern Analysis and Machine Intelligence, Vol. 14, No. 7, July 1992. A maximum modulus line for each zero crossing in the selected frequency band is determine and the peaks are identified as the points where the maximum modulus lines are above a certain threshold depending on the sub-wave to be located. For example, a threshold for an R-peak is selected based on the largest maximum modulus line. Each peak of the selected frequency band that exceeds such a threshold is identified as an R-peak and correlates to an R peak in the EKG signal, or an R sub-wave. Having located the R-peaks in the selected frequency band, a P peak search window preceding each R peak is specified. The size of the P peak search window is based on the RR interval.

For example, the P peak search window may be 50% of the RR interval preceding a specific R peak. The peak having the highest amplitude within the P peak search window is identified as a P peak. Similarly, a T peak search window subsequent to each R peak is specified. For example, the T peak search window may be 25% of the RR interval succeeding each R peak. The peak having the highest amplitude within the T peak search window is identified as a T peak. The peak with the highest amplitude between each P peak and R peak is identified as a Q peak, while the peak with the highest amplitude between each T peak and R peak is identified as a S peak. Thus, by filtering the EKG signal into frequency band, and identifying P, Q, R, S, and T peaks in the selected frequency band, cardiac states are accurately identified. Furthermore, accurate identification of cardiac states is maintained when the heart rate varies.

In addition to each view being correlated, or tagged, with z-location data, each view is also tagged with cardiac phase information determined using the wavelet transforms as described above. Using the projection data from the views tagged with phase and z-location data, a reconstruction technique obtains two-dimensional images of a beating heart at a desired cardiac phase and then reconstructs a three-dimensional image utilizing the two-dimensional image. Any known reconstruction technique can be used to reconstruct a three-dimensional image of a beating heart using the views tagged with phase and z-location data. For example, the filtered back projection technique described in, Principles of Computerized Tomographic Imaging, by A. C. Kak and M. Slaney, IEEE Press, New York N.Y., 1988, can be used.

While the invention has been described in terms of various specific embodiments, those skilled in the art will recognize that the invention can be practiced with modification within the spirit and scope of the claims.

What is claimed is:

1. A method for reconstructing an image of a beating heart, said method comprising:
    decomposing at least one electrocardiogram (EKG) RR interval;
    tagging projection data with cardiac phase information based on the decomposition; and
    reconstructing an image using the tagged data.

2. A method in accordance with claim 1 wherein decomposing at least one EKG comprises dividing each RR interval into a plurality of subwaves.

3. A method in accordance with claim 2 wherein dividing each RR interval comprises applying a wavelet transform to the EKG signal to produce a plurality of frequency bands.

4. A method in accordance with claim 2 wherein decomposing further comprises identifying a plurality peaks in a selected one of the frequency bands.

5. A method in accordance with claim 4 wherein decomposing further comprises:
    identifying at least one of a P peak, a Q peak, a R peak, a S peak and a T peak using the identified peaks in the selected frequency band; and
    determining cardiac phase information based on the at least one of a P, Q, R, S and T peak.

6. A method in accordance with claim 5 wherein tagging projection data further comprises:
    collecting a plurality of projection data utilizing a CT scanning device; and
    correlating the cardiac phase information with each of the projection data collected.

7. A method in accordance with claim 1 wherein reconstructing an image comprises:
    collecting a plurality of projection data for multiple cardiac cycles;
    tagging the projection data collected during each cardiac cycle with cardiac phase information; and
    combining the projection data tagged with like cardiac phase information.

8. A system for reconstructing an image of a beating heart, said system comprising an electrocardiogram (EKG) device, a computed tomography (CT) device electrically coupled to the EKG device, and a processor electrically coupled to at least one of the EKG device and the CT device, said system configured to:
    decompose at least one electrocardiogram (EKG) RR interval;
    determine cardiac phase information based on the decomposition; and
    reconstruct an image using the phase information.

9. A system in accordance with claim 8 wherein to decompose at least one EKG, said system configured to:
    utilize a wavelet transform to produce a plurality of frequency bands; and
    identify a plurality of peaks in a selected one of the frequency bands.

10. A system in accordance with claim 9 wherein to decompose at least one EKG, said system further configured to determine at least one of a P wave, a Q wave, a R wave, a S wave and a T wave within the selected frequency band based on the identified peaks.

11. A system in accordance with claim 10 wherein to determine cardiac phase information, said system further configured to determine cardiac phase information based on the at least one of the P, Q, R, S and T peak.

12. A system in accordance with claim 8 wherein said system further configured to tag projection data with the cardiac phase information.

13. A system in accordance with claim 12 wherein to tag projection data, said system further configured to:
    collect a plurality of projection data utilizing a CT scanning device; and
    correlate at least one of the cardiac phases with each of the projection data collected.

14. A system in accordance with claim 8 wherein to reconstruct an image, said system configured to collect a plurality of projection data for multiple cardiac cycles.

15. A system in accordance with claim 14 wherein to reconstruct an image, said system further configured to:
    tag the projection data collected during each cardiac cycle with cardiac phase information; and
    combine the projection data tagged with like cardiac phase information.

16. A computer readable medium encoded with a program executable by a computer for reconstructing images of a beating heart utilizing data gathered using a computed tomography (CT) device and an electrocardiogram (EKG) device, said program configured to instruct the computer to:
    decompose at least one EKG RR interval into at least one of a P wave, a Q wave,
    a R wave, a S wave, and a T wave; and
    tag projection data with cardiac phase information based on the decomposition.

17. A computer readable medium in accordance with claim 16 wherein to decompose at least one EKG RR interval, said program further configured to instruct the computer to utilize a wavelet transform to extract a plurality of frequency bands from the EKG signal.

18. A computer readable medium in accordance with claim 17 wherein to decompose, said program further configured to instruct the computer to:
   determine peaks in a selected one of the frequency bands; and
   identify at least one of a P peak, a Q peak, a R peak, a S peak, and a T peak based on the determined peaks.

19. A computer readable medium in accordance with claim 18 wherein to tag projection data, said program further configured to instruct the computer to determine cardiac phase information based on the at least one of a P, Q, R, S, and T peak.

20. A computer readable medium in accordance with claim 19 wherein to tag projection data, said program further configured to instruct the computer to correlate the phase information with projection data.

21. A method for determining cardiac phase information used to reconstruct an image of a beating heart, said method comprising:
   decomposing at least one EKG RR interval; and
   determining cardiac phase information based on the decomposition.

22. A method in accordance with claim 21 wherein decomposing comprises applying a wavelet transform to an EKG signal to determine a plurality of frequency bands.

23. A method in accordance with claim 22 wherein decomposing further comprises determining a plurality of peaks within a selected one of the frequency bands.

24. A method in accordance with claim 23 wherein decomposing further comprises identifying at least one of a P peak, a Q peak, a R peak, a S peak, and a T peak based on the plurality of peaks.

25. A method in accordance with claim 21 wherein determining cardiac phase information comprises utilizing the at least one of a P, Q, R, S, and T peak to determine the cardiac phase information.

26. A system for reconstructing an image of a beating heart, said system comprising:
   an electrocardiogram (EKG) device configured to collect EKG data;
   a computed tomography (CT) device electrically coupled to the EKG device configured to acquire projections data; and
   a processor electrically coupled to at least one of the EKG device and the CT device, said processor configured to:
   utilize a wavelet transform to decompose at least one electrocardiogram (EKG) RR interval into a plurality of frequency bands;
   identify a plurality of peaks in a selected one of the frequency bands;
   determine cardiac phase information based on the identified peaks;
   tag projection data with the cardiac phase information; and
   reconstruct an image using the phase information.

27. A system in accordance with claim 26 wherein to utilize a wavelet transform to decompose said processor further configured to determine at least one of a P wave, a Q wave, a R wave, a S wave and a T wave within the selected frequency band based on the identified peaks.

28. A system in accordance with claim 27 wherein to determine cardiac phase information, said processor further configured to determine cardiac phase information based on the at least one of the P, Q, R, S and T peak.

29. A system in accordance with claim 26 wherein to reconstruct and image, said EKG device further configured to acquire a plurality of projection data for multiple cardiac cycles.

30. A system in accordance with claim 26 wherein said system further comprises a reconstructor electrically coupled to at least one of the processor, the CT device, and the processor, wherein to reconstruct an image, said reconstructor configured to combine the projection data tagged with like cardiac phase information.

31. A computer readable medium encoded with a program executable by a computer for reconstructing images of a beating heart utilizing data gathered using a computed tomography (CT) device and an electrocardiogram (EKG) device, said program configured to instruct the computer to:
   utilize a wavelet transform to extract a plurality of frequency bands from the EKG signal;
   determine peaks in a selected one of the frequency bands; and
   identify at least one of a P peak, a Q peak, a R peak, a S peak, and a T peak based on the determined peaks; and
   tag projection data with cardiac phase information based on the decomposition.

32. A computer readable medium in accordance with claim 31 wherein to tag projection data, said program further configured to instruct the computer to:
   determine cardiac phase information based on the at least one of a P, Q, R, S, and T peak; and
   correlate the phase information with projection data.

* * * * *

UNITED STATES PATENT AND TRADEMARK OFFICE
CERTIFICATE OF CORRECTION

PATENT NO. : 6,438,196 B1
DATED : August 20, 2002
INVENTOR(S) : Erdogan Cesmeli

It is certified that error appears in the above-identified patent and that said Letters Patent is hereby corrected as shown below:

Column 7,
Line 50, between "plurality" and "peaks" insert -- of --.

Column 10,
Line 19, delete "and image" and insert therefor -- an image --.
Line 25, delete "processor, the CT" and insert therefor -- EKG, the CT --.

Signed and Sealed this

Twenty-eighth Day of September, 2004

JON W. DUDAS
*Director of the United States Patent and Trademark Office*